US006616618B2

(12) United States Patent
Hagelauer

(10) Patent No.: US 6,616,618 B2
(45) Date of Patent: Sep. 9, 2003

(54) METHOD OF AND DEVICE FOR VISUALIZING THE ORIENTATION OF THERAPEUTIC SOUND WAVES ONTO AN AREA TO BE TREATED OR PROCESSED

(75) Inventor: Ulrich Hagelauer, Bottighofen (CH)

(73) Assignee: Storz Medical AG (CH)

( * ) Notice: Subject to any disclaimer, the term of this patent is extended or adjusted under 35 U.S.C. 154(b) by 0 days.

(21) Appl. No.: 09/805,406

(22) Filed: Mar. 13, 2001

(65) Prior Publication Data

US 2001/0039379 A1 Nov. 8, 2001

Related U.S. Application Data

(63) Continuation of application No. PCT/DE99/02913, filed on Sep. 14, 1999.

(30) Foreign Application Priority Data

Sep. 14, 1998 (DE) .......................................... 198 41 951

(51) Int. Cl.[7] .................................................. A61B 5/03
(52) U.S. Cl. ...................................................... 600/587
(58) Field of Search ................................ 600/439, 437, 600/443, 507, 595; 601/2

(56) References Cited

U.S. PATENT DOCUMENTS

| 4,829,986 A | | 5/1989 | Eichler et al. ................. 128/24 |
| 5,435,311 A | * | 7/1995 | Umemura et al. .......... 600/439 |
| 5,460,595 A | * | 10/1995 | Hall et al. ...................... 601/2 |
| 5,526,814 A | | 6/1996 | Cline et al. ............... 128/653.2 |
| 5,687,737 A | | 11/1997 | Branham et al. ............ 128/710 |
| 5,921,930 A | * | 7/1999 | Uberle ......................... 600/439 |

FOREIGN PATENT DOCUMENTS

| DE | 3811872 | 2/1991 |
| DE | 19512956 | 10/1996 |
| DE | 19515748 | 10/1996 |
| WO | WO91/07726 | 5/1991 |

* cited by examiner

Primary Examiner—Eric F. Winakur
Assistant Examiner—Pamela Wingood
(74) Attorney, Agent, or Firm—St. Onge Steward Johnston & Reens LLC

(57) ABSTRACT

What is described here is a method of and a device for visualizing the orientation of therapeutic sound waves onto a region to be treated or processed, respectively, using a display unit including a screen on which the orientation of said therapeutic sound waves is symbolically displayed with respect to the region to be treated.

The invention excels itself by the provision that the sound wave source and the region in space, through which the sound waves are propagating, as well as the region to be treated or processed (hereinafter referred to as treatment site) are perspectively displayed on said screen by allocation of physical figures, and that the perspective view varies with the correct movement when the site or the orientation of the sound wave source and/or the treatment site and/or the site or the orientation of the screen is varied.

23 Claims, 2 Drawing Sheets

METHOD OF AND DEVICE FOR VISUALIZING THE ORIENTATION OF THERAPEUTIC SOUND WAVES ONTO AN AREA TO BE TREATED OR PROCESSED

This application is a continuation of pending International Application PCT/DE99/02913 filed on Sep. 14, 1999, which designates the United States.

DESCRIPTION

1. Field of the Invention

The present invention relates to a method of visualising the orientation of therapeutic sound waves onto an area to be treated or processed, as well as to a device for carrying through this method.

2. Prior Art

Devices for the application of therapeutic sound waves are generally common:

For lithotripsy, for instance, pulsed pressure or shock waves generated inside or outside the body are employed whereas continuous sound waves are used, for instance, to heat tissue.

It is necessary in any case to direct the therapeutically efficient fraction of the sound field—which will be briefly referred to as "sound wave focus" in the following—onto the region requiring therapeutic treatment or processing, respectively. This may be done by moving the sound source and/or the patient as well as by influencing the distribution of pressure in space within the sound field and hence by displacement of the focus relative to the sound source.

This orientating operation, which will be referred to as "positioning" in the following, should, as a rule, not be performed automatically but by the person applying the device, i.e. a physician, for instance, for a number of reasons such as reasons of liability. To enable the operator to perform such positioning a numerical or graphic indication is required that permits the operator can direct the sound wave focus onto the treatment site.

In lithotripter devices operating on pressure waves generated outside the body the indication is available, for instance, by mixing a crosshair cursor into a two-dimensional X-ray or ultrasonic image.

One solution that is simple from an engineering point of view but possibly inexpedient for the apparatus concept from an ergonomic point of view and with respect to the expenditure incurred by the structure consists in a mechanical connection of the imaging components—i.e. the X-ray tube/image amplifier or the ultrasonic transmitter—to the sound source so as to establish an invariable positional relationship between the imaging components and the ultrasound source.

With more recent developments it has been proposed to arrange the sound source in a mobile form and to detect the spatial positioning of the image-producing or imaging components relative to the sound source by suitable measuring techniques. An example of such a device is described in the German Patent DE-A-195 12 956 to which explicit reference is made with respect to all details not explained here.

As a fixed three-dimensional correlation between the imaging system and the sound source does no longer exist in that device there is no possibility to mix in fixed markers or the like. The position of the sound wave focus, which is now variable, must rather now be displayed or represented relative to the treatment site.

A simple solution in engineering terms consists in a numerical display of this information as spacing in a three-dimensional co-ordinate system. With such a concept, however, positioning becomes a time-consuming operation because the operator is bound to convert this numerical information into a three-dimensional movement.

Another positioning display is described in FIG. 4 of the German Patent DE-A-195 12 959. There the position of the sound wave focus is represented in a plane and on an axis orthogonal on this plane. There is the disadvantage, however, that the operator must permanently keep an eye on two movable markers in order to judge the position in space. Even though misinterpretation is avoided with this display—which is not pseudo three-dimensional—the conversion of the video information does not permit a rapid non-fatiguing positioning.

Moreover, for instance in computer games but not in medical applications—it is the state of the art to generate stereoscopic or pseudo three-dimensional representations by means of two small screens mounted in a helmet: the two screens supply the video information to the left and the right eye separately ("head-mounted displays").

Other known systems use only a single screen on which the video information for the left and the right eye is separated by various techniques ("shutter glasses", polarisation glasses, red/green glasses).

It is known from these applications outside the bioengineering field that all people are not able to gather a three-dimensional impression from stereo displays. But even when a spatial impression can be developed fatiguing occurs after a major period of application, which may result in consequences such as misinterpretation.

For the indication of position in a medical application, however, non-fatiguing operation and reliable protection from misinterpretation must be demanded. After all, the success and the low level of side effects of a therapeutic operation are dependent on the correct conversion of the video information.

BRIEF DESCRIPTION OF THE INVENTION

The present invention is based on the problem of providing a method of visualising the orientation of therapeutic sound waves onto a region to be treated or processed, respectively, as well as a device for carrying through this method, wherein the positioning information is provided by a graphic display easy to interpret.

One inventive method solving this problem is defined in claim 1. Improvements are the subject matters of claims 2 et seq. A device for carrying through the inventive method is defined in claim 23.

The invention starts out from the following finding:

The inventive approach is based on findings gathered in the design of three-dimensional bodies on computers ("computer-aided design", "CAD") and on the application of virtual reality ("VR") based thereon. The basic principle of VR techniques of representation resides in the fact that the perspective of the displayed bodies varies as the viewer's position changes. In distinction from the stereoscopic display the static image alone does not yet create a three-dimensional impression because the left and the right eye receive each the same information.

When, by contrast, a succession of images is generated where the viewer's site is continuously varied the impression is created as if the viewer moves through an arrangement of objects (hereinafter referred to as "scenario").

The human brain is able to conclude the size and the relative position of the displayed objects from such a succession of images. The situation is equal when the viewer is permitted to grasp objects in the scenario apparently (virtual hand) and to move them relative to each other. The similarity of the real scenario with the scenario generated on the screen creates the illusion on the viewer's part as if he were actually in the scenario ("immersion" effect).

It is the basic idea underlying the present invention to utilise such display techniques for positioning the sound wave focus relative to a treatment site.

To this end the sound wave source and the spatial region through which the sound wave are propagating as well as the region to be treated or processed (hereinafter referred to as treatment site) are displayed in a perspective view by assignment of virtual three-dimensional figures. When the site or the orientation of the sound wave source and/or the treatment site and/or the site or the orientation of the screen is varied the perspective view varies equally with the correct movement.

The representation reflects the real position of the sound source and the treatment site in a perspectively correct view so as to provide the operator with a correct impression of the size and the spacings of the figures. For orientation onto the treatment site the figure corresponding to the sound wave focus is moved in the represented scenario just like in reality. The operator therefore gets the impression as if he were in the virtual scenario, guiding the sound source there towards the treatment site (immersion, virtual hand).

It is particularly preferable that the perspective view is changed or can be manually varied when the operator's site varies, in correspondence with the varied view of the scenario for the operator. In particular, the signals representing the position of the sound source in space, which are obtained from a measuring system detecting the relative position of the sound source and the treatment site or the locating means, respectively, are converted into an equivalent virtual movement almost in real time.

In the case of focussed therapeutic sound waves the waves are preferably represented as a cone whose envelope corresponds approximately to the transition between the focussed wave and the marginal diffracted wave. In an improvement, the envelope of the displayed cone is displayed with a surface so open that the treatment site will not be covered. In particular, the envelope of the displayed cone can be represented in a semi-transparent form.

It is furthermore preferred that the treatment site is displayed approximately with the size in which the sound waves produce a therapeutic or processing effect. With focussed sound waves, in particular, the treatment site can be displayed as sphere or ellipsoid.

A particularly preferred embodiment of the inventive method comprises an approach indicator function that represents the approach to or congruence with the region where the sound waves produce a therapeutic or processing effect. Using an additional numerical display or other appropriate means, the operator obtains quantitative information about the precision with which positioning has been performed.

The approach indicator function may be implemented with acoustic means—e.g. by a variation of the pitch (sound frequency) and/or the sound repetition rate. Moreover, the approach indicator function can be implemented by a change of the color in which at least one of the virtual three-dimensional figures is displayed. It is moreover possible to provide the approach indicator function in a numerical form.

To avoid fatiguing it is preferred that the displayed objects present surfaces ("rendering"). In such a case it is expedient to simulate the incidence and reflections of light on the displayed surfaces, for instance in the form in which these effects would occur in the case of an endoscopic or surgical operation.

To this end a virtual source of illumination may be provided on the ceiling of the treatment or processing room. As an alternative or additionally a virtual source of illumination may be arranged in the center of the treatment site. One light source is located above the operator. This corresponds to the light incidence that the operator is accustomed to so that sections illuminated in a brighter color on the cone or sphere surfaces will be estimated as being on top in the correct position. A second light source is located in the middle of the treatment site so that brightening occurs in the area of the tip of the cone when the target is approached. With such a design undesirable strong shading is avoided in an approach to the target from the top.

To facilitate the operator's orientation it is expedient to mix stationary parts of the treatment or processing room into the displayed image. The stationary elements may be a treatment rest and/or a positioning means for a locating means—e.g. an X-ray C arc or an ultrasonic locating means.

It is furthermore expedient for the user that a zoom function is implemented which may be used to display the environment of the treatment site in an enlarged view. Moreover, the position of the treatment site may be displayed as a function of the output signal of a locating means.

BRIEF DESCRIPTION OF THE DRAWING

The invention will be described in the following by exemplary embodiments, without any restriction of the general inventive idea, referring to the drawing which explicit reference is made to in all other respects as far as the disclosure of all inventive details is concerned which are not explained in more details in the text. In the drawing.

DESCRIPTION OF THE EMBODIMENTS

Figure 1:
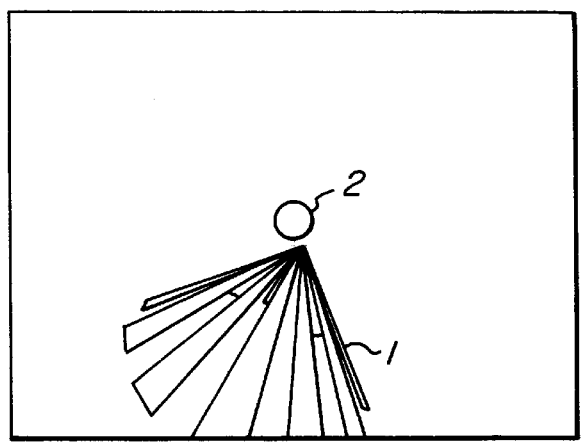
FIG. 1 illustrates the distribution of the sound pressure through an opened cone.

FIG. 1 shows how the distribution of the sound pressure is represented by an opened cone 1. The reference numeral 2 identifies the region onto which the sound field is to be oriented and which is to be caused "to coincide" with the sound wave focus not illustrated in this figure.

In this representation the imagination of the entry cone is made use of, which is mostly imagined by the user. The cone envelope corresponds to the transition between the focussed wave and the marginal diffracted wave, thus representing, in a first approximation, the region in space within which a therapeutically effective sonic energy is transmitted.

The discontinuity of the cone envelope serves to prevent the treatment site 2 from being covered. Another possibility to the same end consists in the semi-transparent representation of the cone ("rendering" in the "transparent mode").

The sound wave focus cannot only be represented as tip of a cone I but can also be descriptively represented in the form of a sphere or an ellipsoid of revolution having a size that corresponds to the size of the sound wave focus. Hence the user is in the position to estimate the achieved positioning accuracy. During the approach of cone 1, the sphere or ellipsoid (sound wave focus) and the treatment site 2 penetrate each other.

Figure 3:
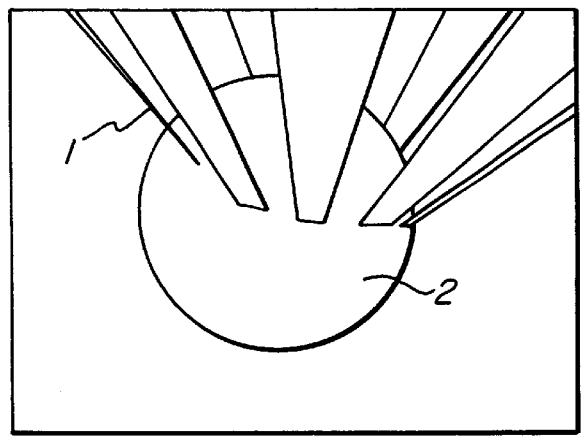
FIG. 3 is a view for explanation of the approach of the therapeutic sound field to the treatment site.

This situation is illustrated in FIG. 3. The resulting overlapping figure permits the conclusion of the relative positions of the sphere and the cone with a precision even higher than the precision in a situation where both objects are displayed at a mutual spacing. Hence the precision in positioning is improved specifically along the last millimeters in the approach, which is desirable in the sense of the application.

Figure 2:
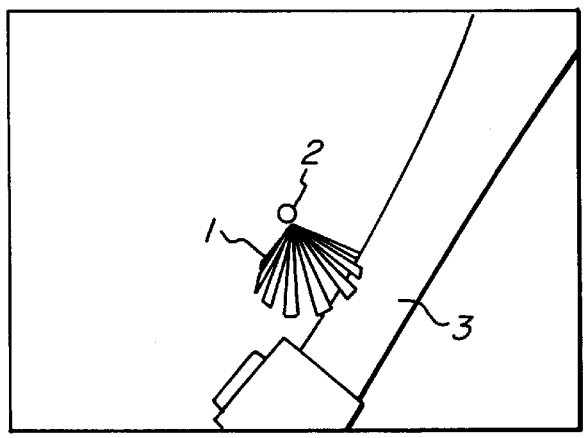
FIG. 2 represents a treatment scenario into which an X-ray C arc has been mixed for an explanation of the possible inputs for the user site.

FIG. 2 explains a possibility of displaying the user's site. To this end a treatment scenario is illustrated in FIG. 2 into which an X-ray C arc 3 has been mixed. The C arc 3 provides the user with an orientation about his site in the scenario. Using mouse control, a touch-responsive screen ("touch screen") or similar means the scenario may be rotated. By comparison against his real site, the user selects the perspective corresponding to his actual position so that he can operate in a real scenario without being forced to make "mental conversions" between the screen display and the actual treatment scenario.

Further possibilities of improving the orientation in space consist in the (additional or alternative) mixing of a treatment rest or other stationary elements at the place of treatment.

It is moreover possible to provide a variable enlargement (zoom function). The enlargement factor is varied as a function of the instantaneous spacing between the tip of the cone and the center of the sphere so that the impression is created on the tip of the cone and the center of the sphere so that the impression is created on the user's part as if he would approach the treatment site himself. On the other hand, this function intensifies the effect of immersion while, on the other hand, the fine tuning along the last millimeters of the approaching distance is improved.

Figure 4:
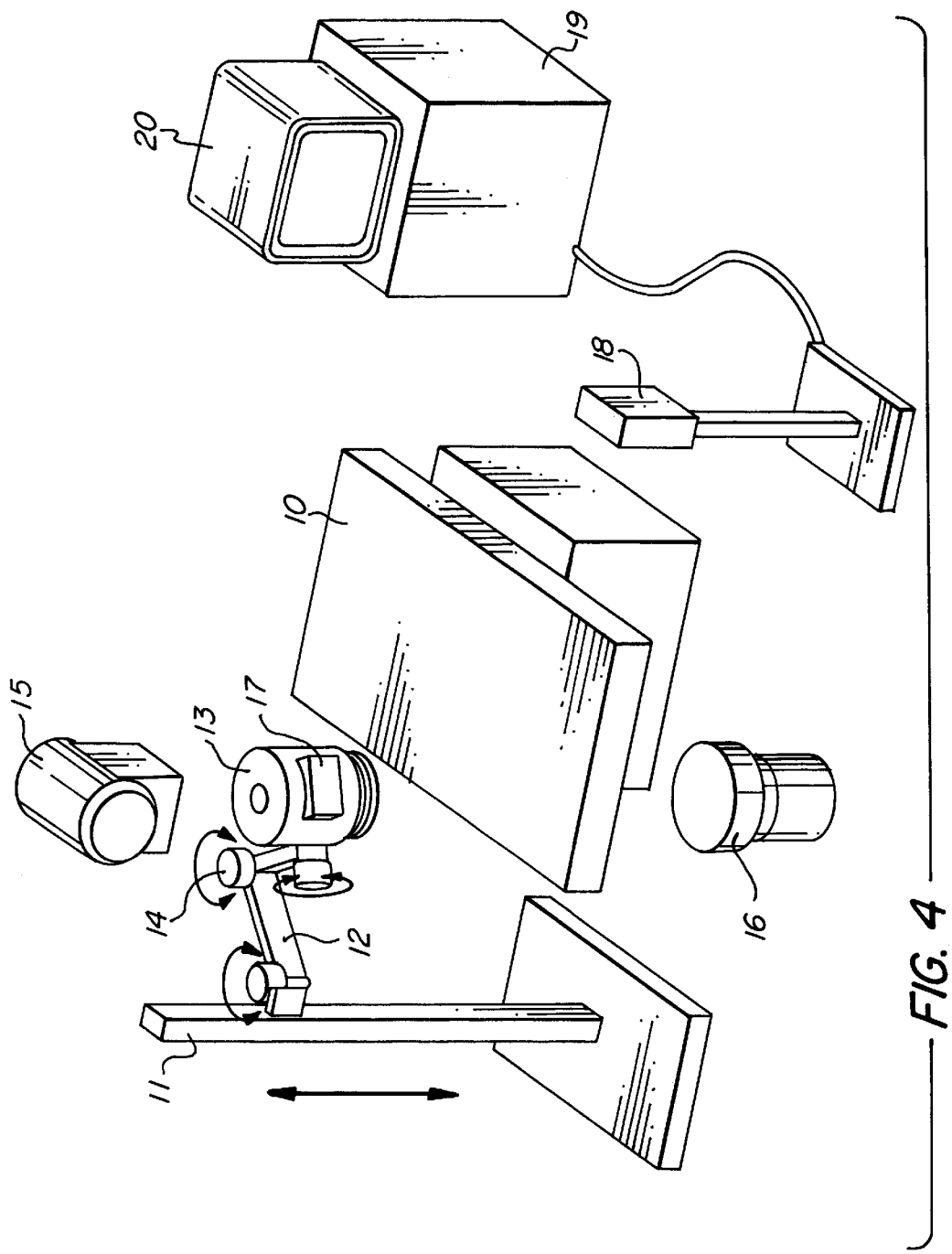
FIG. 4 illustrates a device for carrying through the inventive method.

FIG. 4 shows a typical configuration for a site for treatment with sonic waves in a form improved within the scope of the invention.

The treatment site comprises a patient's rest 10 that is horizontally displaceable, vertically adjustable and/or rotatable, in a manner known per se, for positioning a patient who is not illustrated here. An adjustable supporting arm 12 for holding a therapeutic sound source 13 is mounted on a support 11. The sound source may be configured in a manner known per se and be intended, for instance, for destroying concrements, for pain treatment, for treatment of the heart, for heating regions of the body, or the like. It should be made clear explicitly that the foregoing enumeration of potential configurations of the sound source of its applications is not final.

The reference numeral 14 denotes a braking means for decelerating the movements of the sound source 13, which permits a precise adjustment of the sound source 13 relative to the patient or the patient's rest, respectively. The sound source 13 can hence be positioned in the desired manner relative to a patient resting on the rest 10 either by hand or possibly by using a servo adjuster.

An X-ray tube 15 with an image amplifier 16, which may be mounted, for instance, on a C arc not illustrated here, serves to detect the region requiring treatment, e.g. a concrement in the kidney, the bladder or the urinary tract in a patient resting on the rest 10. Additionally, or as an alternative, it is also possible to provide other locating systems such as ultrasonic location systems.

A sensor 17 is mounted on the sound source 13, which permits the detection of the position of the sound source 13 relative to the patient's rest 13 or the detected region on the patient to be treated by means of a position detector system 18 that produces an output signal applied to an analysis and controller unit, e.g. a computer system 19 including a screen 20 on which, by application of the inventive method, suitable information is displayed for an operator—i.e. in the case of medical applications a physician. What is not displayed are appropriate input means such as a keyboard, a mouse control, a touch screen or voice control of the system 19.

During the treatment procedure the position detector system 18 supplies continuously data on the position of the sound source 13 relative to the rest 10 to the controller and analysis unit or the computer system 19, respectively.

The computer programme of the computer system 19 encompasses high-speed algorithms for computing the perspective ("VR" programmes), for generating a surface ("rendering") and for calculation of light reflection ("ray tracing"). Such programmes are known from other—non-medical—applications such as CAD applications so that here the configuration of such programmes need not be discussed in more details. The scenario displayed on the screen 20 is updated several times per second on the basis of the positional data so that the real-time simulation is achieved that is required for immersion.

At the same time it is also possible to detect other objects such as the image amplifier 16 of the X-ray apparatus or an ultrasonic transmitter, and to display them as well in the scenario for better orientation. It is equally possible to use the same computer system to read images for input, such as those provided by the X-ray system ("frame grabber") and to determine the position of the treatment site in space on the basis of the position of the image amplifier in two projections, as is described in the German Patent DE-A-195 12 956.

Quantitative information about the distance between the tip of the cone and the center of the sound wave focus can be transmitted in various ways. It is possible, for example, to mix in a numerical display of the distance.

Another possibility is an audible signal sounding at a lower repetition rate at a wider distance. As the distance is decreasing the repetition rate is continuously increased. When the distance drops below a predetermined spacing the pitch is raised.

A third possibility consists in a change of the color of the cone and/or the sphere, which takes place continuously or when the distance drops below a predetermined value. Moreover provisions may be made for the generation of a signal acting upon the braking means 14 for decelerating the movements of the sound source 13, in response to a drop below a predetermined spacing from the target.

A further improvement envisaged as a solution consists in having the positional signal acting upon a motor adjustment means of the sound source 13 or in influencing the distribution of the pressure of the sound source in space, both for automation of the positioning operation.

Another embodiment provides for a basic three-dimensional representation of the interior of the body as starting point, as it may be obtained, inter alia, by CT, NMR or ultrasonic examination. The cone figure may be superimposed onto this display in order to represent the position of the sound wave field relative to anatomic structures. This feature is suitable to improve the therapy and to reduce side effects, e.g. by avoiding that gas-filled cavities or bone structures are within the sound field.

The aforedescribed method is, of course, also suitable for application in fields other than medicine, e.g. in materials processing where a focussed wave field (of any wave type whatsoever) is employed whose focus is to be caused to coincide with a processing site.

What is claimed is:

1. Method of visualizing the orientation of therapeutic sound waves on to a region to be treated or processed, comprising the steps of:

providing a display unit including a screen, symbolically displaying the orientation of the therapeutic sound waves in relation to the region to be treated on said screen, perspectively displaying the sound wave source and the region in space, through which the sound waves are propagating, as well as the region to be treated or processed on said screen by allocation of virtual three-dimensional figures, and characterized in that the representation reproduces the real position of said sound source and said treatment site in a perspectively correct form so as to create a correct impression of the size and the spacing of the figures, that for orientation onto the treatment site the figure corresponding to the sound wave field moves in exactly the same manner as in reality, and that the perspective view varies with the correct movement when the site or the orientation of the sound wave source and/or the treatment site and/or the site or the orientation of the screen is varied.

2. Method according to claim 1, characterized in that perspective view varies or can be manually varied when the site of an operator varies, in correspondence with the variation of the operator's view.

3. Method according to claim 1, characterized in the case of focused therapeutic sound waves these waves are displayed as a cone whose envelope corresponds to the transition between the focused wave and a marginal diffracted wave.

4. Method according to claim 3, characterized in that the envelope of the displayed cone is represented with a surface so opened that the treatment site will not be covered.

5. Method according to claim 3, characterized in that the envelope of the displayed cone is represented in a semi-transparent form.

6. Method according to claim 1, characterized in that the treatment site is displayed in the same size in which the sound waves produce a therapeutic or processing effect.

7. Method according to claim 6, characterized in that with focused sound waves the treatment site is displayed as a sphere or ellipsoid.

8. Method according to claim 1, characterized in that an approach indicator function is provided which indicates the approach to or congruence with the region in which the sound waves produce a therapeutic or processing effect.

9. Method according to claim 8, characterized in that said approach indicator function produces an audible signal.

10. Method according to claim 9, characterized in that said approach indicator function signals by a variation of the pitch and/or the sound repetition rate.

11. Method according to claim 8, characterised in that said approach indicator function signals by a change of the color in which at least one of said virtual three-dimensional figures is displayed.

12. Method according to claim 8, characterized in that said approach indicator function signals by a numerical indication.

13. Method according to claim 1, characterized in that light incidence and light reflection are simulated on the displayed surfaces.

14. Method according to claim 13, characterized in that a virtual illumination source is disposed on the ceiling of a treatment or processing room.

15. Method according to claim 13, characterized in that a virtual illumination source is disposed in the center of the treatment site.

16. Method according to claim 1, characterized in that said approach indicator function signals by a change of the color in which at least one of said virtual three-dimensional figures is displayed.

17. Method according to claim 16, characterized in that stationary elements are provided, the stationary elements being a treatment rest and/or a positioning means for a locating means.

18. Method according to claim 17, characterized in that said positioning means is an X-ray C arc.

19. Method according to claim 1, characterized in that a zoom function is provided which serves to represent the environment of the treatment site in an enlarged view.

20. Method according to claim 1, characterized in that the position of the treatment site is displayed as a function of the output signal of a locating means.

21. Apparatus for carrying through the method according to claim 1, characterized in that a position detector system is provided that detects the position of said sound source relative to the region requiring therapy or processing, and whose output signal is applied to an analysis and controller unit including a screen on which the mutual assignment between the sound wave focus and the region requiring treatment or processing, respectively, is displayed in a perspective view by the assignment of virtual three-dimensional figures.

22. Method of rendering visible an orientation of therapeutic sound waves with respect a treatment site of a body of a patient to be treated, comprising the steps of:

displaying the orientation of the therapeutic sound waves in relation to the treatment site symbolically on a screen of a display unit;

allocating virtual three-dimensional figures to a sound wave source, a sound wave field in space through which the sound waves are propagating, and the treatment site, and displaying said figures in perspective on said screen;

representing a position of said sound wave and said treatment site in correct perspective to create a correct impression of a size and spacing of the figures;

moving the figure corresponding to the sound wave field in the same manner as in reality when orienting the sound wave field with respect to the treatment site; and changing the perspective view correctly in accordance with movement occurring with a variation of at least one of the following: the position of the sound wave source, and orientation of the sound wave source, the treatment site, a site of the screen, and an orientation of the screen.

23. Method of rendering visible an orientation of focused sound waves with respect a processing site of a material to be processed, comprising the steps of:

displaying the orientation of the sound waves in relation to the processing site symbolically on a screen of a display unit;

allocating virtual three-dimensional figures to a sound wave source, a sound wave field in space through which the sound waves are propagating, and the processing site and displaying said figures in perspective on said screen;

representing a position of said sound wave source and said processing site in correct perspective to create a correct impression of a size and spacing of the figures;

moving the figure corresponding to the sound wave field in the same manner as in reality when orienting the sound wave field with respect to the processing site; and changing the perspective view correctly in accordance with movement occurring with a variation of at least one of the following; the position of the sound wave source, an orientation of the sound wave source, the processing site, a site of the screen, and an orientation of the screen.

* * * * *